(12) United States Patent
Moon et al.

(10) Patent No.: US 12,714,552 B2
(45) Date of Patent: Aug. 25, 2026

(54) BREAST IMPLANT HAVING WAVINESS

(71) Applicant: HANS BIOMED CORP, Seoul (KR)

(72) Inventors: Dae Hee Moon, Daejeon (KR); Young Jik Lee, Daejeon (KR); Myeong Hun Bae, Daejeon (KR); Da Eun Seo, Daejeon (KR)

(73) Assignee: HANS BIOMED CORP, Seoul (KR)

( * ) Notice: Subject to any disclaimer, the term of this patent is extended or adjusted under 35 U.S.C. 154(b) by 892 days.

(21) Appl. No.: 18/016,302

(22) PCT Filed: Mar. 2, 2021

(86) PCT No.: PCT/KR2021/002572

§ 371 (c)(1),
(2) Date: Jun. 14, 2023

(87) PCT Pub. No.: WO2022/014814

PCT Pub. Date: Jan. 20, 2022

(65) Prior Publication Data

US 2023/0301771 A1 Sep. 28, 2023

(30) Foreign Application Priority Data

Jul. 17, 2020 (KR) ........................ 10-2020-0089178

(51) Int. Cl.
*A61F 2/12* (2006.01)
*A61F 2/00* (2006.01)

(52) U.S. Cl.
CPC ........ *A61F 2/12* (2013.01); *A61F 2002/0081* (2013.01)

(58) Field of Classification Search
CPC .. A61F 2/12; A61F 2002/0081; A61F 2/0077; A61L 2400/18; A61L 2430/04; A61L 2400/02
See application file for complete search history.

(56) References Cited

U.S. PATENT DOCUMENTS

| | | | |
|---|---|---|---|
| 4,573,999 | A | 3/1986 | Netto |
| 8,556,968 | B2 | 10/2013 | Hamas et al. |
| 11,369,467 | B2 | 6/2022 | Quiros et al. |
| 11,446,131 | B2 | 9/2022 | Harvie |

(Continued)

FOREIGN PATENT DOCUMENTS

| | | |
|---|---|---|
| KR | 10-2014-0089425 A | 7/2014 |
| KR | 10-2018-0091769 A | 8/2018 |

(Continued)

OTHER PUBLICATIONS

Breast Implant Surfaces and their impact on current practices, Munhoz et al (Year: 2019).*

(Continued)

*Primary Examiner* — Bruce E Snow
(74) *Attorney, Agent, or Firm* — Procopio, Cory, Hargreaves & Savitch LLP

(57) ABSTRACT

The present application relates to a breast implant having surface roughness and waviness. A breast implant according to an aspect includes: a shell constituting an outer skin; and a filler material accommodated inside the shell, wherein an outer surface of the shell has a concave-convex surface in contact with tissue, and the surface has a certain level of waviness in a filtered waviness curve.

12 Claims, 5 Drawing Sheets

(56) References Cited

U.S. PATENT DOCUMENTS

| | | | |
|---|---|---|---|
| 2019/0125401 | A1 | 5/2019 | Chacon Quiros et al. |
| 2019/0290382 | A1 | 9/2019 | Martinez et al. |
| 2020/0046489 | A1 | 2/2020 | Feinberg et al. |
| 2020/0170771 | A1* | 6/2020 | Bayat .................... G03F 7/0037 |
| 2020/0188078 | A1* | 6/2020 | Bayat .................. H01J 37/3056 |
| 2022/0142762 | A1 | 5/2022 | Hill et al. |

FOREIGN PATENT DOCUMENTS

| | | | |
|---|---|---|---|
| KR | 10-2018-0103873 | A | 9/2018 |
| KR | 10-2019-0008252 | A | 1/2019 |
| KR | 10-2019-0142772 | A | 12/2019 |
| KR | 10-2206018 | B1 | 1/2021 |
| WO | 2017/196973 | A2 | 11/2017 |
| WO | 2020/070676 | A1 | 4/2020 |
| WO | 2020/070694 | A1 | 4/2020 |

OTHER PUBLICATIONS

Extended European Search Report issued in European Patent Application No. EP 21842462.0, dated Jul. 3, 2024, 8 pages.

International Search Report and Written Opinion of the International Searching Authority for the corresponding PCT Application No. PCT/KR2021/002572 dated Jun. 9, 2021, 10 pages.

* cited by examiner

BREAST IMPLANT HAVING WAVINESS

TECHNICAL FIELD

The present application relates to a breast implant having waviness.

BACKGROUND ART

Many people currently undergo transplantation of medical implants for medical or cosmetic purposes. Breast implants have been used for reconstruction and augmentation of the breast, and can be classified as saline-filled, silicone gel-filled, hydrogel-filled, and PVP-filled breast implants, depending on the filler material. To reduce side effects caused by foreign body reactions that occur at the time of transplantation of foreign substances, breast implants are undergoing a generational shift toward securement of biosafety. As an example of side effects of breast implants, capsular contracture, which occurs when a hard capsule is formed around an implant and shrinks, is representative. When capsular contracture occurs, problems of breast hardening, damage in appearance, and discomfort are caused.

The silicone gel-filled implant of the early first generation were of the smooth type with a considerable thickness of an outer skin and a smooth surface. Although the rate of rupture of the outer skin was low, silicone leakage was severe and capsular contracture around the implant was caused, making it difficult to secure biosafety. Then, the silicone gel-filled implant of the second generation was a smooth type with a thin outer skin. As the outer skin becomes thin, the occurrence of capsular contracture was reduced, but an increase in ruptures was still a problem. In the silicone gel-filled implant of the third generation, a multi-layered outer skin type with a barrier layer was introduced to reduce silicone leakage, and a shape was given to the surface, so that a development toward a reduction in the capsular contracture was made. The surface shape applied for the first time was a textured type having a hole shape on the outer skin, and due to this type of surface, an implant could be firmly positioned with the breast tissue after transplantation, and accordingly the occurrence of capsular contracture was significantly reduced. Since then, various types of breast implants have been developed for a natural form and a soft touch, but recently, cases of occurrence of breast implant-associated anaplastic large cell lymphoma (BIA-ALCL), which is a type of hematologic malignancy, in the textured-type implants have been reported, and thus safety management of breast implants is being strengthened.

Currently, the International Standards Organization (ISO) classifies the surface of breast implants into three types, i.e., a smooth type, a micro-texture type, and a macro-texture type, according to surface roughness, and is implementing a suspension of sales of all breast implant products that have a macro-texture surface corresponding to the previous textured surface type. To improve such continuous issues with biosafety, an interest in the implant surface is increasing in the field of breast implant technology. The surface of a breast implant should be similar to the living tissue to have less foreign body reaction, and should be attached to the surrounding tissue to enable positioning of the breast implant in the correct site. At this time, an excessive reaction with the surrounding tissue can cause side effects, such as capsular contracture, capsulation, BIA-ALCL, and the like, and thus the development of an appropriate surface is needed. Under this background, a variety of studies are ongoing on breast implants that do not cause BIA-ALCL after insertion into the body and thus have excellent biocompatibility and safety (KR 10-2014-0089425), but the situation is still incomplete.

DISCLOSURE

Technical Problem

An aspect provides a breast implant including: a shell constituting an outer skin; and a filler material accommodated inside the shell, wherein the shell has surface characteristics showing surface roughness and a certain level of waviness.

Other purposes and advantages of the present disclosure will become more obvious with the following detailed description, claims, and drawing. Contents not described herein will be sufficiently recognized and inferred by those skilled in the technical field of the present application or in a similar technical field therewith, and thus descriptions of such contents will be omitted.

Technical Solution

Description and embodiments disclosed herein may also be applied to other descriptions and embodiments, respectively. That is, all combinations of various elements disclosed herein belong to the scope of the present disclosure. In addition, the scope of the present application is not construed to be limited by the detailed description provided below.

An aspect provides a breast implant comprising: a shell constituting an outer skin; and a filler material accommodated inside the shell, wherein an outer surface of the shell has a concave-convex surface in contact with tissue, and the surface has an arithmetic mean waviness (Wa) value of 3.00 μm or more in a waviness curve filtered under a measurement condition with a cut-off value of 0.08.

The term "implant" as used in the present specification is a general term for grafts or implants that can be used in skin depressions or areas grooved by wrinkles and to improve volume for cosmetic purposes. The term "breast implant 100" as used herein is a general term for implants that can be transplanted in a patient undergoing surgery and treatment related to the breast, and the inner side of the breast implant 100 may be filled with a filler material. In addition, the breast implant 100 may be a round type or an anatomical type depending on the shape.

The term "shell 110" as used herein is an exterior part of an implant that is manufactured to replace the breast tissue, and refers to a structure that is in the shape of a flexible thin film, and can also change the overall shape of the breast implant 100 according to the flow of a filler material. The shell 110 may primarily serve as a pocket that can be filled with a fluid material, i.e., a filler material 120, inside the shell. In addition, secondarily, the surface characteristics of the outermost shell adjacent to tissue may not only affect the adhesive strength between the implant 100 and the tissue, but also play a role in regulating biological reactions such as an inflammatory reaction and the like.

The shell 110 may be prepared according to a method known in the art. In an embodiment, the shell 110 may be prepared by the steps comprising: preparing a mandrel having characteristics with a certain level of waviness and surface roughness; preparing and curing a shell by repeating a process of dipping the prepared mandrel in a medical solution and drying the same multiple times; and separating the cured shell from the mandrel. However, embodiments are not limited thereto.

The shell 110 may be formed of, for example, a biocompatible material including silicone, polyester, or the like, and preferably, a silicone material or a silicone polymer material. However, any material that is non-toxic to the living body and capable of imparting effective surface characteristics may be applied widely without limitation.

The term "filler material 120" as used in the present specification may consist of saline, hydrogel, silicone gel, or other fluids having appropriate fluidity, and in some cases, a material of other textures or properties (e.g., a sponge) may be added to alleviate or suppress the fluidity of the fluids.

Meanwhile, in breast augmentation using a breast implant, breast implant-associated anaplastic large cell lymphoma (BIA-ALCL) has emerged as the biggest issue. The BIA-ALCL was caused in the Allergan's textured breast implant, and in fact, the sales of all silicone implant products related to the BIAL-ALCL have been suspended in Europe. Accordingly, various studies on the above subject are in the process, but nothing has been mentioned about the relationship between the occurrence of the BIA-ALCL and the surface waviness of breast implants.

As shown in FIG. 1, the breast implant 100 according to an embodiment or a shell thereof may have surface characteristics showing a certain level of waviness along with surface roughness at the same time. In addition, FIG. 2 is a diagram schematically showing the state of the breast implant 100 according to an embodiment after being inserted into the body. The breast implant 100 having the aforementioned characteristics may be inserted in a state that the surface is in contact with at least one tissue selected from the group consisting of thin fascia, muscular fascia, breast fascia, supportive fiber, and transverse fibrolamella.

The term "waviness 111" as used in the present specification refers to a surface curvature with a relatively long period compared to a roughness curve of the surface of the breast implant 100, and is commonly used interchangeably with "W" or "Wmax". The waviness 111 is also defined by a distance between two parallel lines that are parallel to the centerline of the cross-sectional curve and that touch the highest peak and the deepest valley, by taking as much as the standard length of waviness from the cross-sectional curve. In detail, under a measurement condition with a cut-off value of 0.08 mm, a cross-sectional curve, i.e., a height profile curve, recorded by enlarging the contour appearing in a cross-section perpendicular to the measurement plane of the breast implant 100 in the vertical and horizontal directions, is obtained, and then, the waviness 111 can be calculated from a curve filtered by passing only a frequency less than the cut-off frequency. In addition, the waviness parameter may be related to the adhesive strength throughout target tissue among the surrounding tissue into which the breast implant 100 is inserted.

Meanwhile, since a surface of an actual breast implant has a very complicated and diverse appearance, a measurement result can be affected depending on a portion to be measured. In this regard, the term "cut-off value" as used in the present specification refers to a reference length selected by a filter when the mean of waviness or surface roughness is directly measured by using a measuring method known in the art, such as a measuring method using a stylus electrical measuring device, a 3D laser scanning method, and the like. Typically, as the cut-off value, 0.08 mm, 0.25 mm, 0.8 mm, 2.5 mm, 8 mm, and 25 mm are selected as reference lengths, and unless otherwise specified in the present specification, the cut-off value may be 0.08 mm.

The term "arithmetic mean waviness (Wa)" as used in the present specification refers to an arithmetic mean height of waviness curve, and the parameter value may be defined according to the ISO 25178-2:2012 standard.

In an embodiment, the surface may have the arithmetic mean waviness (Wa) value of 3.00 μm or more in a waviness curve filtered under a measurement condition with a cut-off value of 0.08. The arithmetic mean waviness (Wa) value may be, for example, in a range of 3.00 μm to 7.00 μm, 3.07 μm to 7.00 μm, or 3.50 μm to 6.00 μm. In addition, the arithmetic mean waviness (Wa) value may be, for example, in a range of 3.50 μm to 7.00 μm, 3.50 μm to 6.50 μm, 3.50 μm to 6.00 μm, 3.50 μm to 5.50 μm, 3.50 μm to 5.00 μm, 3.50 μm to 4.50 μm, 3.50 μm to 4.00 μm, 4.00 μm to 7.00 μm, 4.00 μm to 6.50 μm, 4.00 μm to 6.00 μm, 4.00 μm to 5.50 μm, 4.00 μm to 5.00 μm, 4.00 μm to 4.50 μm, 4.50 μm to 7.00 μm, 4.50 μm to 6.50 μm, 4.50 μm to 6.00 μm, 4.50 μm to 5.50 μm, 4.50 μm to 5.00 μm, 5.00 μm to 7.00 μm, 5.00 μm to 6.50 μm, 5.00 μm to 6.00 μm, 5.00 μm to 5.50 μm, 5.50 μm to 7.00 μm, 5.50 μm to 6.50 μm, 5.50 μm to 6.00 μm, 6.00 μm to 7.00 μm, or 6.00 μm to 6.50 μm. When the arithmetic mean waviness (Wa) value is out of the ranges above and is lower than the ranges above, the surface is excessively smooth, and thus the possibility of occurrence of capsular contracture and fibrosis increases. Meanwhile, when the arithmetic mean waviness (Wa) value is higher than the ranges above, an increase in the possibility of occurrence of BIA-ALCL is concerned.

The term "maximum height (Wz) of waviness curve" as used in the present specification refers to an arithmetic mean height of waviness curve, and the parameter value may be defined according to the ISO 25178-2:2012 standard.

In an embodiment, the surface may have a maximum height (Wz) value of 19.16 μm or more in a waviness curve filtered under a measurement condition with a cut-off value of 0.08. The maximum height (Wz) value may be, for example, in a range of 20.00 μm to 44.00 μm. In addition, the maximum height (Wz) value may be, for example, in a range of 20.00 μm to 40.00 μm, 20.00 μm to 35.00 μm, 20.00 μm to 30.00 μm, 20.00 μm to 25.00 μm, 25.00 μm to 44.00 μm, 25.00 μm to 40.00 μm, 25.00 μm to 35.00 μm, 25.00 μm to 30.00 μm, 30.00 μm to 44.00 μm, 30.00 μm to 40.00 μm, or μm 30.00 to 35.00 μm. When the maximum height Wz value is out of the ranges above, there is also a possibility that the aforementioned problems may occur.

The term "surface roughness 112" as used in the present specification refers to unevenness with a short period and a relatively small amplitude on the surface of the breast implant 100. For example, under a measurement condition with a cut-off value of 0.08 mm, a cross-sectional curve, i.e., a height profile curve, recorded by enlarging the contour appearing in a cross section perpendicular to the measurement plane of the breast implant 100 in the vertical and horizontal directions, is obtained, and then, the surface roughness 112 can be calculated from a curve filtered by passing only a frequency exceeding a cut-off frequency. In addition, the surface roughness parameter may be related to the adhesive strength of local tissue among the surrounding tissue into which the breast implant 100 is inserted. Meanwhile, the parameter value may be measured according to the ISO 14607:2018 standard and calculated according to the ISO 25178-2:2012 standard.

The term "arithmetic mean roughness (Ra)" as used in the present specification refers to an arithmetic mean height of roughness curve, and the parameter value may be defined according to the ISO 25178-2:2012 standard.

In an embodiment, the surface may have the arithmetic mean roughness (Ra) value of 1.00 μm or more in a waviness curve filtered under a measurement condition with a cut-off value of 0.08. The arithmetic mean roughness (Ra) value may be in a range of 1.09 μm to 2.00 μm, for example, 1.09 μm to 1.90 μm, 1.09 μm to 1.80 μm, 1.09 μm to 1.70 μm, 1.09 μm to 1.60 μm, 1.09 μm to 1.50 μm, 1.09 μm to 1.40 μm, 1.09 μm to 1.30 μm, 1.09 μm to 1.20 μm, 1.20 μm to 2.00 μm, 1.20 μm to 1.90 μm, 1.20 μm to 1.80 μm, 1.20 μm to 1.70 μm, 1.20 μm to 1.60 μm, 1.20 μm to 1.50 μm, 1.20 μm to 1.40 μm, 1.20 μm to 1.30 μm, 1.30 μm to 2.00 μm, 1.30 μm to 1.90 μm, 1.30 μm to 1.80 μm, 1.30 μm to 1.70 μm, 1.30 μm to 1.60 μm, 1.30 μm to 1.50 μm, 1.30 μm to 1.40 μm, 1.40 μm to 2.00 μm, 1.40 μm to 1.90 μm, 1.40 μm to 1.80 μm, 1.40 μm to 1.70 μm, 1.40 μm to 1.60 μm, 1.40 μm to 1.50 μm, 1.50 μm to 2.00 μm, 1.50 μm to 1.90 μm, 1.50 μm to 1.80 μm, 1.50 μm to 1.70 μm, 1.50 μm to 1.60 μm, 1.60 μm to 2.00 μm, 1.60 μm to 1.90 μm, 1.60 μm to 1.80 μm, 1.60 μm to 1.70 μm, 1.70 μm to 2.00 μm, 1.70 μm to 1.90 μm, 1.70 μm to 1.80 μm, 1.80 μm to 2.00 μm, 1.80 μm to 1.90 μm, or 1.90 μm to 2.00 μm. The arithmetic roughness (Ra) value can be applied to the breast implant 100 along with the aforementioned waviness value at the same time. When the arithmetic mean roughness (Ra) value is out of the ranges above and is lower than the ranges above, the surface is excessively smooth, and thus the possibility of occurrence of capsular contracture and fibrosis increases. Meanwhile, when the arithmetic roughness Ra value is higher than the ranges above, problems of an increase in the possibility of occurrence of BIA-ALCL exist.

The term "maximum height (Rz) of roughness curve" as used in the present specification refers to an arithmetic mean height of roughness curve, and the parameter value may be defined according to the ISO 25178-2:2012 standard.

In an embodiment, the surface may have a maximum height (Rz) value of 5.84 μm or more in a roughness curve filtered under a measurement condition with a cut-off value of 0.08. The maximum height (Rz) value may be, for example, in a range of 5.84 μm to 10.29 μm. In addition, the maximum height (Rz) value may be, for example, in a range of 5.84 μm to 10.00 μm, 5.84 μm to 8.00 μm, 5.84 μm to 6.00 μm, 6.00 μm to 10.00 μm, or 6.00 μm to 8.00 μm. When the maximum height (Rz) value is out of the ranges above, there is also a possibility that the aforementioned problems may occur.

Meanwhile, the surface of the breast implant 100 according to an embodiment may have at least one of the following characteristics:

(a) arithmetic mean waviness (Wa) value in a range of 3.07 μm to 7.00 μm in a waviness curve filtered under a measurement condition with a cut-off value of 0.08;

(b) maximum height (Wz) value in a range of 20.00 μm to 44.00 μm in a waviness curve filtered under a measurement condition with a cut-off value of 0.08;

(c) arithmetic mean roughness (Ra) value in a range of 1.09 μm to 2.00 μm in a roughness curve filtered under a measurement condition with a cut-off value of 0.08; and (b) maximum height (Rz) value in a range of 5.84 μm to 10.29 μm in a roughness curve filtered under a measurement condition with a cut-off value of 0.08.

In addition, the surface of the breast implant 100 according to an embodiment may have a skewness (Wsk) value in a range of −0.48 μm to 0.41 μm and a kurtosis (Wku) value in a range of 2.62 μm to 5.28 μm in the waviness curve filtered under a measurement condition with a cut-off value of 0.08. In one or more embodiments, the surface may have a skewness (Rsk) value in a range of −0.21 μm to 0.22 μm and a kurtosis (Rku) value in a range of 2.72 μm to 3.86 μm in the roughness curve filtered under a measurement condition with a cut-off value of 0.08. However, embodiments are not limited thereto.

As described above, by having a certain level of waviness along with surface roughness at the same time, the breast implant 100 may improve, among the surrounding tissue into which the breast implant is inserted, not only the adhesive strength to a local area, but also the adhesive strength to a wider area at the same time. In this regard, the adhesive strength between the breast implant 100 and the surround tissue can be significantly improved, and accordingly, an inflammatory reaction of the surrounding tissue can be alleviated, and ultimately, the formation of BIL-ALCL caused by breast augmentation can be suppressed.

In addition, regarding the breast implant 100, technical elements, such as a shell thickness, a type and an amount of a filler material, a types and a shape of an adhesive patch, a volume of an implant, and the like, other than the surface characteristics of the breast implant 100 or the shell 110, can be applied without limitation by using techniques known in the art.

Advantageous Effects

In the breast implant according to an aspect, the shell surface has a certain level of waviness along with surface roughness at the same time, and such surface characteristics can contribute to improving adhesion between the breast implant and living tissue. Therefore, the breast implant according to an aspect can provide excellent biocompatibility and high stability by reducing the formation of BIA-ALCL which is a conventional side effect.

BEST MODE

Hereinafter, the present disclosure will be described in detail with reference to Examples below. However, these Examples are provided for illustrative purposes only, and the scope of the present disclosure is not limited thereto.

Preparation Example 1. Preparation of Breast Implant According to Embodiment In the present reparation Example, a breast implant having surface characteristics with a certain level of waviness along with surface roughness was prepared. In detail, after preparing a mandrel housing formed of an aluminum material that is surface-treated by a sandblasting method, a surface of the mandrel was coated with polytetrafluoroethylene (Teflon) to prepare a mandrel having arithmetic mean waviness and arithmetic mean roughness Ra values in a specific range. Afterwards, by repeating a process of dipping the prepared mandrel into a medical solution and drying the same multiple times, a shell of the breast implant was cured, and the cured shell was separated from the mandrel and was turned over again to obtain the shell of the breast implant according to an embodiment. Then, a filler material filled the inside region of the shell to prepare a breast implant according to an embodiment.

Figure 1:
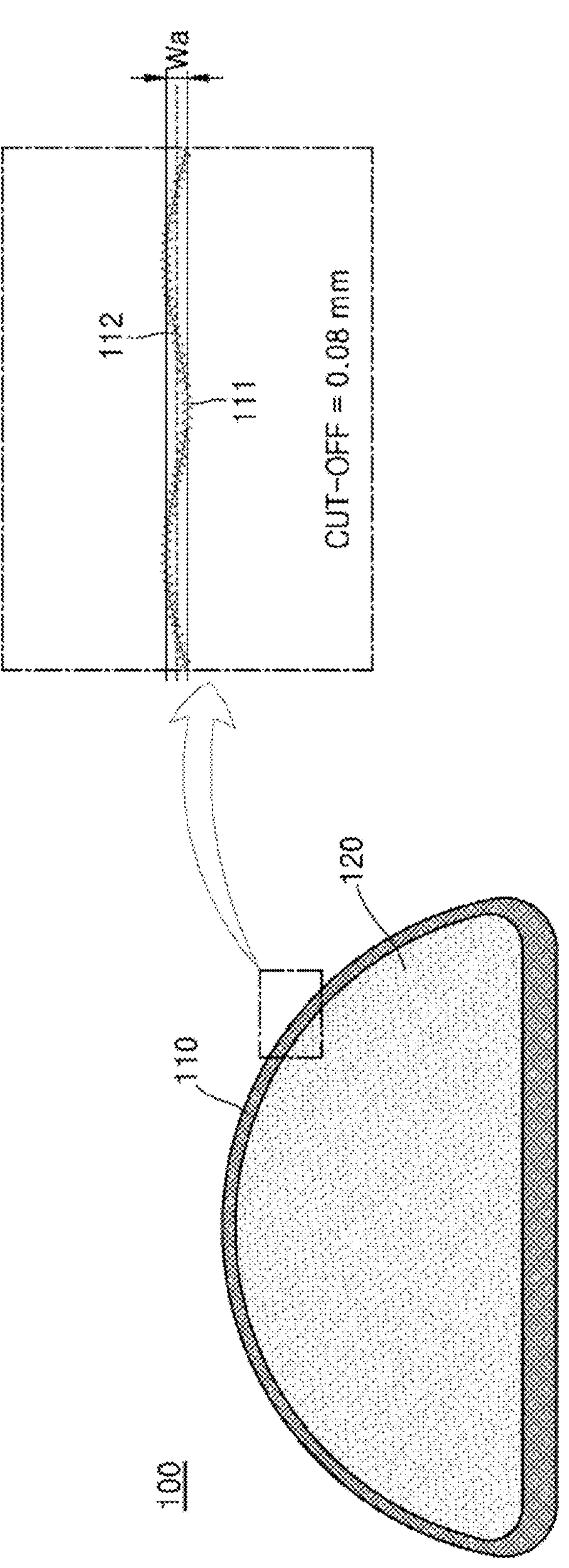
FIG. 1 is a diagram showing a breast implant according to an embodiment and a shell surface thereof.
Figure 2:
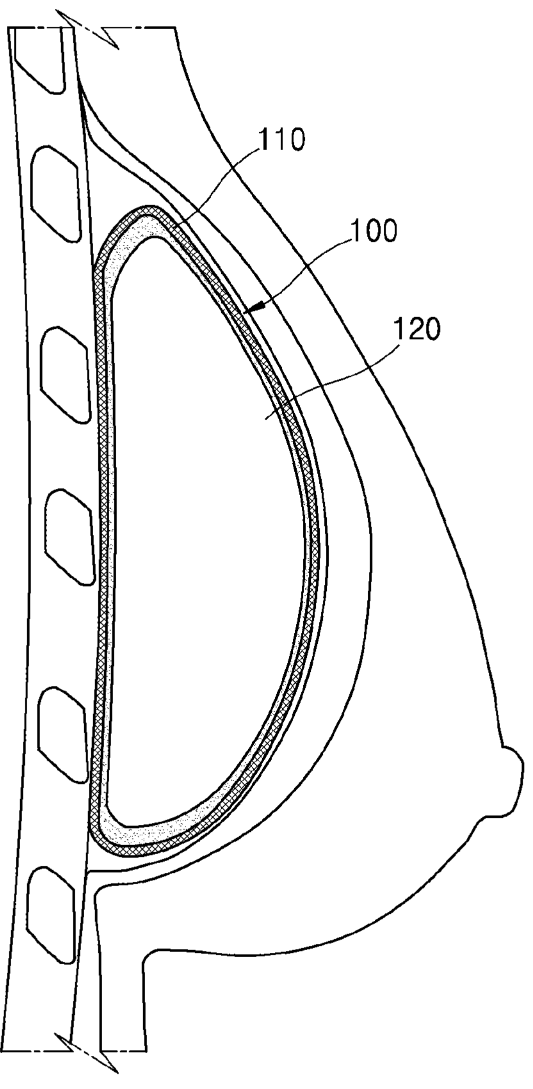
FIG. 2 is a diagram schematically illustrating a state of a breast implant according to an embodiment after being inserted into a body.
Figure 3:
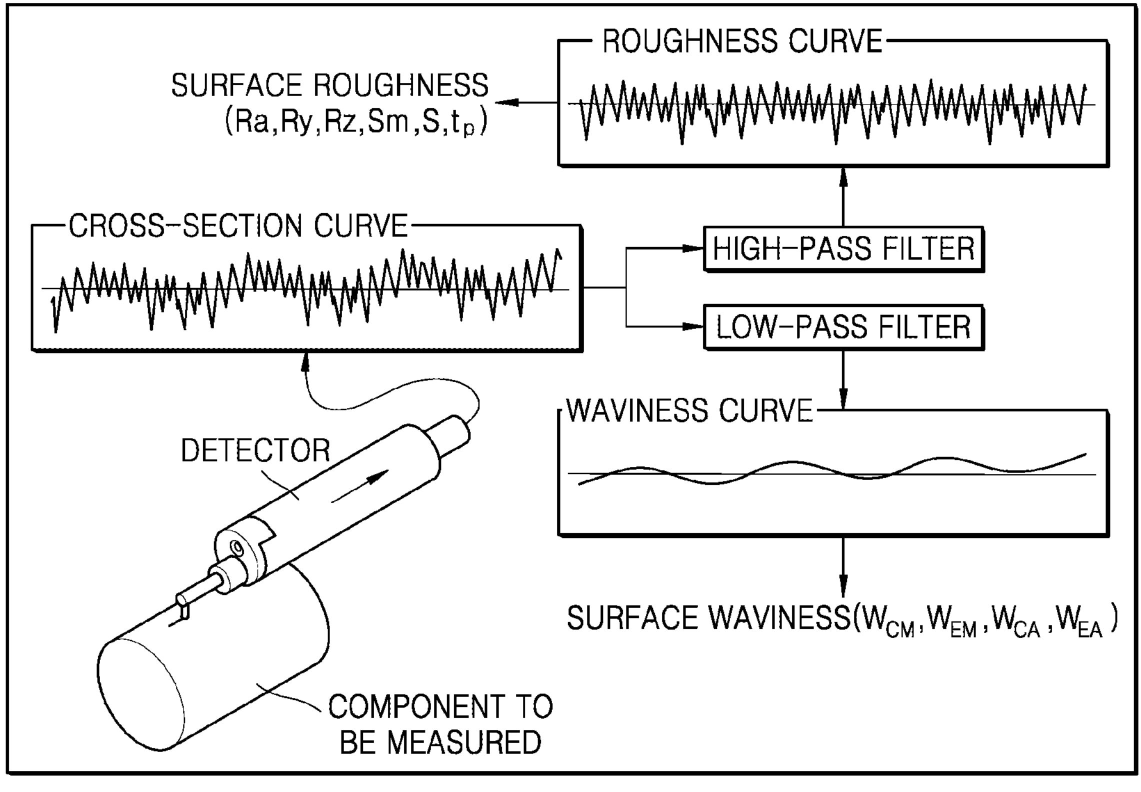
FIG. 3 is a diagram schematically illustrating a process of measuring surface roughness and waviness of a shell surface of a breast implant according to an embodiment.

Experimental Example 1. Evaluation of Surface Characteristics of Breast Implant According to Embodiment In the present Experimental Example, the surface characteristics, specifically, surface roughness and waviness, of the prepared breast implant were evaluated. In detail, as shown in FIG. 3, after measuring a height profile (cross-sectional curve) of the surface of the breast implant, based on the measured height profile distribution, a roughness profile filtered by passing only frequencies exceeding the cut-off frequency, and a waveform profile filtered by passing only frequencies below the cut-off frequency were obtained, respectively. Then, by analyzing the roughness profile and the waveform profile, the surface roughness and waviness of the breast implant were evaluated. Meanwhile, in the present experiment, the surface roughness and waviness were measured according to the ISO 14607:2018 standard by using a 3D laser microscope (Olympus OLS5000), and then calculated according to the ISO 25178-2:2012 standard. The evaluation of the surface characteristics was measured at a cut-off value of 0.08 mm, and a conventional product was used as a comparison group.

1. Evaluation of Waviness

Figure 4:
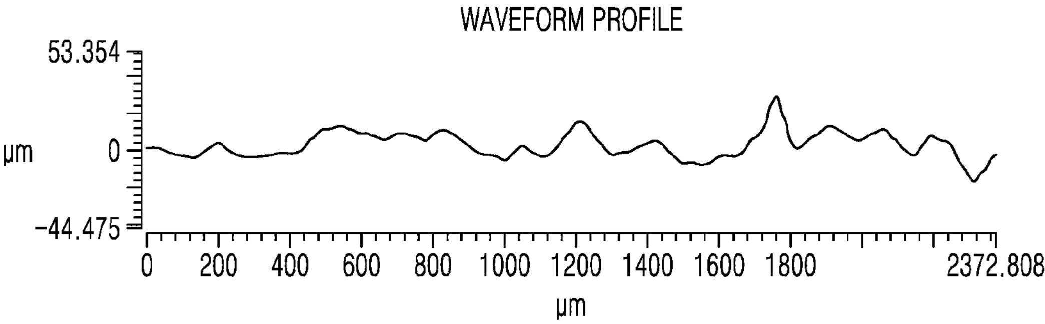
FIG. 4 shows a result of a waveform profile under a measurement condition of a cut-off value of 0.08 with respect to a shell surface of a breast implant according to an embodiment.
Figure 5:
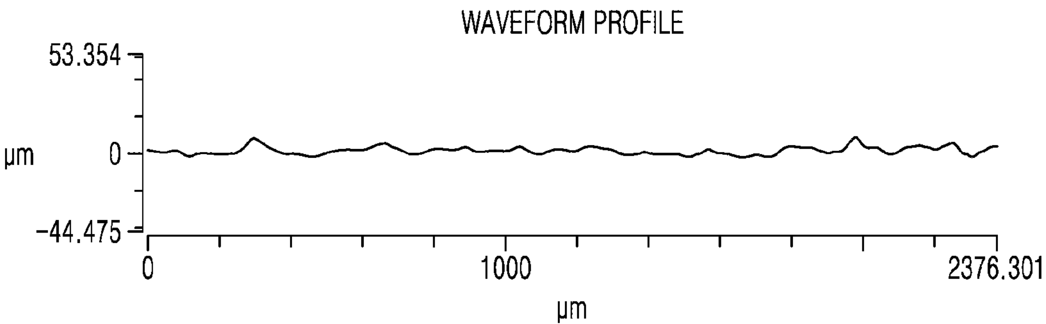
FIG. 5 is a result showing a waveform profile under a measurement condition of a cut-off value of 0.08 with respect to the shell surface of a breast implant according to a Comparative Example.

Based on the height profile data, FIGS. 4 and 5 show results of obtaining waveform profiles with respect to the shell surfaces of the breast implants according to Example 1 and Comparative Example 1. In addition, the results of evaluating the waviness of each of the breast implants according to an Example and a Comparative Example that were measured in the same way as the above, are shown in Table 1 below.

TABLE 1

| Division | Wa | Wz | Wsk | Wku |
|---|---|---|---|---|
| Example 1 | 5.358 | 31.440 | 0.407 | 2.719 |
| Example 2 | 3.074 | 19.160 | 0.045 | 2.768 |
| Example 3 | 3.789 | 21.684 | −0.141 | 2.622 |
| Example 4 | 4.121 | 24.004 | −0.267 | 2.634 |
| Example 5 | 4.888 | 32.638 | −0.344 | 2.803 |
| Example 6 | 5.993 | 43.979 | 1.15 | 5.272 |
| Example 7 | 6.386 | 42.853 | −0.481 | 3.296 |
| Comparative Example 1 | 1.629 | 9.856 | 0.605 | 2.889 |
| Comparative Example 2 | 7.598 | 61.358 | 0.086 | 5.193 |

(unit: μm)

As a result, as shown in Table 1, it was confirmed that the breast implant according to an embodiment showed a clear difference in the arithmetic mean waviness (Wa) value and the maximum height (Wz) value compared to the breast implant of the comparison group.

Based on these experimental results, it was found that the surface of the breast implant according to an embodiment had waviness, that is, surface curvature characteristics under the corresponding experimental conditions. That is, in the present experiment, the experiment was conducted on the breast implant having the arithmetic mean waviness (Wa) value in a range of about 3 μm to about 7 μm and the maximum height (Wz) value in a range of about 9 μm to about 61 μm.

2. Evaluation of Surface Roughness

Figure 6:
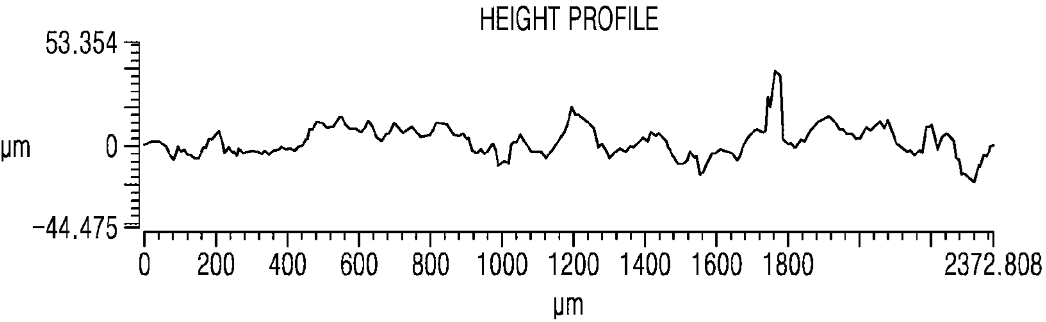
FIG. 6 shows a result of a height profile under a measurement condition of a cut-off value of 0.08 with respect to a shell surface of a breast implant according to an embodiment.
Figure 7:
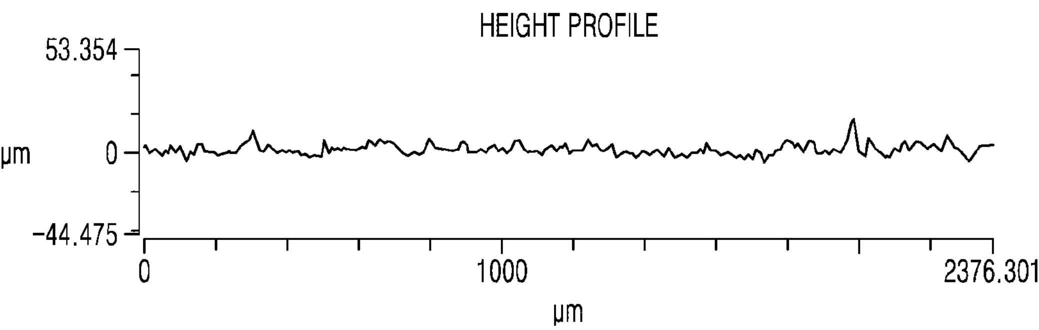
FIG. 7 is a result showing a roughness profile under a measurement condition of a cut-off value of 0.08 with respect to a shell surface of a breast implant according to a Comparative Example.
Figure 8:
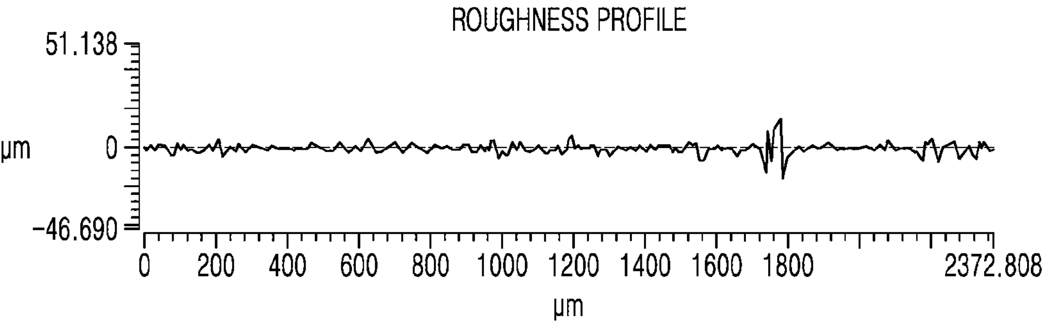
FIG. 8 shows a result of a roughness profile under a measurement condition of a cut-off value of 0.08 with respect to a shell surface of a breast implant according to an Example.
Figure 9:
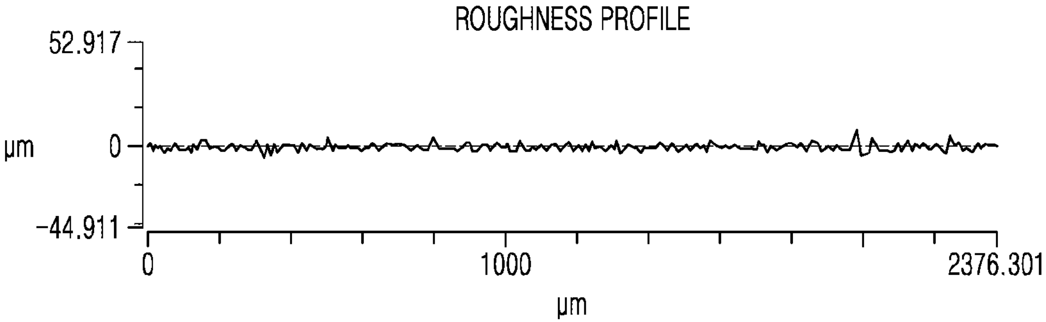
FIG. 9 is a result showing a roughness profile under a measurement condition of a cut-off value of 0.08 with respect to a shell surface of a breast implant according to a Comparative Example.

FIGS. 6 and 7 show results of height profiles under a measurement condition with a cut-off value of 0.08 with respect to the shell surfaces of the breast implants according to Example 1 and a Comparative Example. In addition, based on the height profile data, FIGS. 8 and 9 show results of obtaining roughness profiles with respect to the shell surfaces of the breast implants according to Example 1 and Comparative Examples. In addition, the results of evaluating the roughness of each of the breast implants according to Examples and Comparative Examples, measured in the same way, are shown in Table 2 below.

TABLE 2

| Division | Ra | Rz | Rsk | Rku |
|---|---|---|---|---|
| Example 1 | 1.091 | 6.815 | 0.181 | 3.548 |
| Example 2 | 1.468 | 9.01 | 0.037 | 3.404 |
| Example 3 | 1.722 | 10.285 | −0.183 | 3.015 |
| Example 4 | 1.079 | 5.845 | 0.068 | 2.722 |
| Example 5 | 1.465 | 7.607 | −0.217 | 2.914 |
| Example 6 | 1.045 | 6.778 | 0.049 | 3.854 |
| Example 7 | 1.671 | 8.998 | 0.222 | 2.978 |
| Comparative Example 1 | 1.095 | 6.448 | 0.146 | 3.063 |
| Comparative Example 2 | 1.341 | 8.249 | −0.029 | 3.423 |

(unit: μm)

As a result, as shown in Table 2, the breast implants according to an embodiment and a Comparative Example showed the distribution with the arithmetic mean roughness (Ra) value in a range of about 1.04 μm to about 1.72 μm and the maximum height (Rz) value in a range of about 5.84 μm to about 10.29 μm.

Experimental Example 2. Preparation of Animal Model for Silicone-Filled Implant 8-week-old SD rats were anesthetized with a combination of respiratory anesthesia and injection anesthesia before surgery (2 rats per experimental group, 18 rats in total). Before inserting an implant, a surgery site was thoroughly sterilized with betadine, and about a 3 cm incision was made on the back. After the incision, a pocket for implant insertion was formed, and a circular implant with a diameter of 2 cm [Examples 1 to 7 and Comparative Examples 1 and 2] was inserted. After the insertion, the incision site was sutured. After 16 weeks, biopsies were collected and analyzed.

Experimental Example 3. FACS Surface Protein Analysis

The cells obtained in Experimental Example 1 were collected and washed with PBS. Afterwards, the resultant cells were put into a lysis buffer. While vortexing the buffer solution, a reaction was allowed at 4° C. for 1 hour, followed by centrifugation. Then, the supernatant was quantified with a BCA solution. After subjecting 50 μg of the protein to electrophoresis with 12% gel and being transferred to a nitrocellulose paper, blocking with 10% skim milk was performed thereon for 1 hour. Afterwards, cytokines and antibodies to various transcription factors were treated thereon for 1 hour, and then washed with PBS-tween. After treating each with secondary antibodies for 30 minutes, followed by washing, an ECL solution kit was used to detect and obtain data of neoplastic cells, ALK−, and CD30+. The results are shown in Table 3 below.

TABLE 3

| Division | Neoplastic cells | ALK− | CD30+ |
|---|---|---|---|
| Example 1 | − | − | − |
| Example 2 | − | − | − |
| Example 3 | − | − | − |
| Example 4 | − | − | − |
| Example 5 | − | − | − |
| Example 6 | − | − | − |
| Example 7 | − | − | − |
| Comparative Example 1 | − | − | − |
| Comparative Example 2 | + | + | + |

As a result, as shown in Table 3, it was confirmed that neoplastic cells, ALK−, and CD30+, which are significant ALCL-related factors, were not detected in the breast implants according to Examples 1 to 7. In addition, these experimental results were remarkable compared to the breast implant according to Comparative Example 2.

Experimental Example 4. Gene Expression Analysis Using RT-PCR

After finely incising the biopsy, an easy-Blue solution was added for homogenization, and chloroform was added to perform centrifugation. 400 μl of the supernatant was mixed with the same amount of ethanol, and the resulting solution was centrifuged and washed with 70% ethanol. After subjecting to air dry, DEPC water was added thereto, RNA was quantified, and then cDNA was synthesized. Afterwards, each primer and a polymerase were added for amplification. To confirm expression of mRNA, the amplification product was subjected to electrophoresis using an agarose gel. Accordingly, results for the Ahr cell surface proteins were obtained. The results are shown in Table 4 below.

TABLE 4

| Division | Ahr |
|---|---|
| Example 1 | + |
| Example 2 | + |
| Example 3 | + |
| Example 4 | + |
| Example 5 | + |
| Example 6 | + |
| Example 7 | + |
| Comparative Example 1 | + |
| Comparative Example 2 | +++ |

As a result, as shown in Table 4, it was confirmed that the expression of the Ahr cell surface protein, which is an ALCL-related factor, was suppressed by the breast implants according to Examples 1 to 7, resulting in ALCL-negative results, whereas the expression level of Ahr was an ALCL positive level in the breast implant according to Comparative Example 2.

Experimental Example 5. Collagen Density Analysis Using Masson's Trichrome (MT) Staining After MT staining was performed according to the protocols of the manufacturer (Polysciences, Pennsylvania, USA), collagen density was measured. The results are shown in Table 5 below.

TABLE 5

| Division | Collagen density (%) |
|---|---|
| Example 1 | 55 |
| Example 2 | 58 |
| Example 3 | 57 |
| Example 4 | 55 |
| Example 5 | 53 |
| Example 6 | 54 |
| Example 7 | 52 |
| Comparative Example 1 | 67 |
| Comparative Example 2 | 50 |

As a result, as shown in Table 5, it was confirmed that the collagen density in the breast implants according to Examples 1 to 7 was in a range of 52% to 58%, whereas the collagen density in the breast implant according to Comparative Example 1 was at a level significantly higher than that of Examples.

The foregoing descriptions are only for illustrating the present disclosure, and it will be apparent to a person having ordinary skill in the art to which the present invention pertains that the embodiments disclosed herein can be easily modified into other specific forms without changing the technical spirit or essential features. Therefore, it should be understood that Examples described herein are illustrative in all respects and are not limited.

EXPLANATION OF REFERENCE NUMERALS

100: BREAST IMPLANT
110: SHELL
111: WAVINESS
112: SURFACE ROUGHNESS
120: FILLER MATERIAL

The invention claimed is:

1. A breast implant comprising: a shell constituting an outer skin; and a filler material accommodated inside the shell, wherein an outer surface of the shell has a concave-convex surface, and the surface has an arithmetic mean waviness (Wa) value of 3.07 μm to 7.00 μm in a waviness curve filtered under a measurement condition with a cut-off value of 0.08 mm.

2. The breast implant of claim 1, wherein the arithmetic mean waviness (Wa) value is in a range of 3.50 μm to 6.00 μm.

3. The breast implant of claim 1, wherein the surface has a maximum height (Wz) value of 19.16 μm or more in the waviness curve filtered under a measurement condition with a cut-off value of 0.08 mm.

4. The breast implant of claim 3, wherein the maximum height (Wz) value is in a range of 20.00 μm to 44.00 μm in the filtered waviness curve.

5. The breast implant of claim 1, wherein the surface has an arithmetic mean roughness (Ra) value of 1.00 μm or more in a roughness curve filtered under a measurement condition with a cut-off value of 0.08 mm.

6. The breast implant of claim 5, wherein the arithmetic mean roughness (Ra) value is in a range of 1.09 μm to 2.00 μm.

7. The breast implant of claim 1, wherein the surface has a maximum height (Rz) value of 5.84 μm or more in a roughness curve filtered under a measurement condition with a cut-off value of 0.08 mm.

8. The breast implant of claim 7, wherein the maximum height (Rz) value is in a range of 5.84 μm to 10.29 μm in the filtered roughness profile.

9. The breast implant of claim 1, wherein the surface has a skewness (Wsk) value in a range of −0.48 μm to 0.41 μm and a kurtosis (Wku) value in a range of 2.62 μm to 5.28 μm in a waviness curve filtered under a measurement condition with a cut-off value of 0.08 mm.

10. The breast implant of claim 1, wherein the surface has a skewness (Rsk) value in a range of −0.21 μm to 0.22 μm and a kurtosis (Rku) value in a range of 2.72 μm to 3.86 μm in a roughness curve filtered under a measurement condition with a cut-off value of 0.08 mm.

11. The breast implant of claim 1, wherein the shell is formed of silicone material.

12. The breast implant of claim 1, wherein the breast implant suppresses breast implant-associated anaplastic large cell lymphoma (BIA-ALCL).

* * * * *